United States Patent [19]

Wang et al.

[11] 4,205,015

[45] May 27, 1980

[54] DEHYDROHALOGENATION OF (POLYHALOALKYL) BENZENES WITH SUPPORT LEWIS ACID CATALYSTS

[75] Inventors: Chun S. Wang; Stanley D. McGregor; Terry J. Nestrick, all of Midland, Mich.

[73] Assignee: The Dow Chemical Company, Midland, Mich.

[21] Appl. No.: 906,893

[22] Filed: May 18, 1978

[51] Int. Cl.$^2$ .............................................. C07C 25/00
[52] U.S. Cl. ............................ 260/651 R; 260/651 F
[58] Field of Search ........................ 260/651 R, 651 F

[56] References Cited

U.S. PATENT DOCUMENTS

| | | | |
|---|---|---|---|
| 2,404,538 | 7/1946 | Schmerling et al. | 260/669 R |
| 2,561,516 | 7/1951 | Ladd et al. | 260/651 R |
| 2,725,411 | 11/1955 | Ladd et al. | 260/654 |
| 2,899,473 | 4/1959 | LePrince et al. | 260/666 |
| 3,299,152 | 1/1967 | Inaba et al. | 260/654 D |
| 3,300,533 | 1/1967 | Keith et al. | 260/651 R |

FOREIGN PATENT DOCUMENTS 1087334 10/1967 United Kingdom ............ 260/677 XA

*Primary Examiner*—Delbert E. Gantz
*Assistant Examiner*—Joseph A. Boska

[57] ABSTRACT

A process for the dehydrohalogenation of a (polyhaloalkyl)benzene containing a benzylic halogen such as 1,3-dichloro-5-(2,4,4,4-tetrachlorobutyl)-benzene by contacting the (polyhaloalkyl)benzene with a Lewis acid such as $AlCl_3$ deposited on an inert support such as silica gel or alumina under conditions sufficient to catalyze said dehydrohalogenation to form a (polyhaloalkenyl)benzene such as 3,5-dichloro-α-(2,2,2-trichloroethyl)styrene.

6 Claims, No Drawings

DEHYDROHALOGENATION OF (POLYHALOALKYL) BENZENES WITH SUPPORT LEWIS ACID CATALYSTS

BACKGROUND OF THE INVENTION

This invention relates to processes for preparing (haloalkenyl)benzenes including (polyhaloalkenyl)benzenes.

α-(1-Haloalkyl)styrenes are taught in U.S. Pat. No. 3,391,203 to be useful as parasiticides and insecticides. They are also known to be useful intermediates in the manufacture of other biologically active compounds. Such compounds are conventionally prepared by reacting a halogenated organic compound with an α-methylstyrene in the presence of a free-radical initiator which usually comprises an organic amine and a copper-containing material. Unfortunately, these known methods for preparing haloalkenylbenzenes require long reaction times and undesirably high reaction temperatures and give somewhat low yields of product.

In view of the deficiencies of prior art methods, it would be highly desirable to provide an improved method for making haloalkenylbenzenes.

SUMMARY OF THE INVENTION

In accordance with the present invention, (haloalkenyl)benzenes and other (haloalkenyl)arenes are advantageously obtained by a dehydrohalogenation process, which comprises contacting a (polyhaloalkyl)arene in which polyhaloalkyl has a benzylic halogen and at least one non-benzylic aliphatic halogen with a catalytic amount of a suitably active Lewis acid deposited on an inert solid particulate support (hereinafter called supported Lewis acid) under dehydrohalogenation conditions. Surprisingly, the benzylic halogen of the polyhaloalkyl group is selectively eliminated to form the desired (haloalkenyl)arene while the non-benzylic aliphatic halogen(s) are left undisturbed. Even more surprising is the fact that the resulting (haloalkenyl)arenes can be readily reacted with peroxide or other suitable oxygen source to epoxidize the carbon-to-carbon double bond of the haloalkenyl group. The (haloalkenyl)benzenes produced in the practice of this invention are useful as biologically active compounds as described hereinbefore and as intermediates in the preparation of other biologically active compounds.

DETAILED DESCRIPTION OF THE EMBODIMENTS

For the purposes of this invention, a (polyhaloalkyl)arene is an aromatic compound in which an aromatic ring bears at least one polyhaloalkyl substituent. In said polyhaloalkyl substituent, one halogen is bonded to the alkyl carbon bonded to the aromatic ring (hereinafter called a benzylic halogen) and at least one halogen is bonded to one other alkyl carbon (hereinafter called a non-benzylic halogen). By "arene" is meant an aromatic compound having one or more aromatic rings such as benzene, naphthalene, anthracene as well as substituted arenes. The substituent or substituents of such substituted arenes include halo, nitro, alkyl, alkoxy, alkylthio, aryl, aryloxy, sulfo, carboxy, carboxylate ester, haloalkyl including polyhaloalkyl, haloaryl and other substituent-groups which do not interfere with dehydrohalogenation reactions which are catalyzed by Lewis acids. Accordingly, such substituents are inert in such dehydrogenation reactions.

Preferred (polyhaloalkyl)arenes, for the purposes of this invention, are represented by Formula (I):

wherein Ar is arene, preferably benzene, each R is individually halo, alkyl, haloalkyl, including polyhaloalkyl such as —CX$_3$ (e.g., —CF$_3$) and

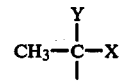

wherein X and Y are as defined herein, aryl, haloaryl, nitro, alkoxy, and other inert monovalent organic radicals, X is halo, Y is haloalkyl or substituted haloalkyl wherein alkyl has from 2 to 3 carbons and the substituent or substituents may be nitro, alkoxy and the like, n is 0 to the maximum number of remaining available ring positions on Ar, preferably n is from 0 to 2 when Ar is benzene. More preferably, each R is individually halo such as Cl, Br, or F; alkyl having 1-to 4 carbons such as —CH$_3$; alkoxy such as —OCH$_3$ and others having 1 to 4 carbons; and —NO$_2$. Most preferably each R is individually Cl, Br or —NO$_2$. X is more preferably Cl or Br, most preferably Cl. Y is more preferably haloalkyl represented by the formula:

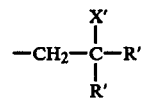

wherein X' is Cl or Br, each R' is individually H, halo such as Cl, Br or F, lower alkyl or —NO$_2$. Most preferably Y is —CH$_2$CCL$_2$R' wherein R' is H, Cl, Br, —CH$_3$ or —C$_2$H$_5$. For example, Y is most preferably —CH$_2$CCl$_3$, —CH$_2$CCl$_2$Br, —CH$_2$CHCl$_2$ and —CH$_2$CH$_2$Cl.

Examples of especially preferred poly(haloalkyl)arenes include 1,3-dichloro-5-(2,4,4,4-tetrachlorobutyl)benzene, 1,3-dichloro-5-(2,4,4-trichlorobutyl)benzene and similar 1,3-dihalo-5-(polyhalobutyl)benzenes. Other preferred (polyhaloalkyl)arenes include 3-chloro-1-(2,4,4,4-tetrachlorobutyl)benzene and similar 3-halo-1-(polyhalobutyl)benzenes.

(Polyhaloalkyl)arenes are suitably prepared by any known method. For example, α-methylstyrene or ar-substituted methylstyrene prepared in accordance with one of the procedures described in U.S. Pat. No. 2,816,934 to Stempel is reacted with a polyhaloalkane such as carbon tetrachloride, bromotrichloromethane, methylene chloride or dichloronitromethane in the presence of an amine and cuprous chloride by the procedure described in U.S. Pat. No. 3,454,657 to produce a desired (polyhaloalkyl)benzene.

Lewis acids which are suitably employed in the practice of this invention are the Lewis acids which, when deposited on a solid support, catalyze the elimination of the benzylic halogen from the (polyhaloalkyl)arene via a dehydrohalogenation reaction while essentially all of the non-benzylic halogen substituent(s) of the (polyhaloalkyl)arene remain bonded to the (polyhaloalkyl)arene. Such suitable Lewis acids are stated herein to be suitably active if, during the preferential dehydrohalogenation of essentially all (>95 mole percent) of benzylic halogen of the (polyhaloalkyl)arene, less than 10, preferably less than 3, mole percent of non-benzylic halogen is eliminated.

Most common Lewis acids such as AlCl$_3$, FeCl$_3$, SnCl$_4$ and the like are suitably active when deposited on a solid catalyst carrier or support. Examples of such Lewis acids which in supported form are suitably active include the halides, particularly the chlorides and bromides, of such metals as aluminum, iron, zinc, copper, antimony, titanium, bismuth, arsenic, tantalum, vanadium, magnesium, boron and tin; as well as the oxyhalides, oxides, sulfates, phosphates, nitrates and oxylates of such metals. Of the foregoing Lewis acids, the halides, especially the chlorides, of aluminum, titanium, iron and antimony are most preferably employed in combination with a solid particulate catalyst support.

Exemplary solid catalyst supports include silica, silica gel, titania, alumina, silica/alumina, magnesia, asbestos, charcoal, fuller's earth, diatomaceous earths, vanadia magnesium silicate, bauxite, dausonite, gibbsite, Florida earth, bentonite, kaolin, pipe clay, montmorillonite, kieselguhr and the like. Of the foregoing supports, silica gel and alumina are preferred. Advantageously, the catalyst support is in the form of a particulate solid, preferably one having an average particle diameter in the range from about 100 to about 400 micrometers and a surface area in the range from about 80 to about 200 square meters per gram.

The supported Lewis acid is advantageously prepared by slurrying the support in a solution of the desired Lewis acid in an inert organic solvent such as hydrocarbon or halogenated hydrocarbon solvents, e.g., carbon tetrachloride (CCl$_4$), dichloromethane, chloroform, methylchloroform and tetrachloroethylene. Alternatively, both Lewis acid and support can be slurried in an organic diluent which does not dissolve the Lewis acid or the support. In either case, from about 0.1 to about 3 weight parts of Lewis acid and from about 1 to about 30 weight parts of solid support are added to 100 weight parts of organic liquid. Advantageously, the resulting slurry is heated at about the reflux temperature, e.g., from about 50° to about 80° C., of the organic liquid for a time sufficient to cause deposition of the Lewis acid on the support, usually from about 10 to about 60 minutes. While the concentration of Lewis acid in the total supported catalyst (i.e., the supported Lewis acid) is not particularly critical, the Lewis acid preferably constitutes from about 5 to about 15 weight percent of the total supported catalyst with the remainder being the solid support.

In the practice of the dehydrohalogenation process of this invention, the (polyhaloalkyl)arene is contacted with a catalytic amount of a suitably active Lewis acid under dehydrohalogenation conditions. A catalytic amount is any amount of suitably active Lewis acid which catalyzes the selective dehydrohalogenation of the (polyhaloalkyl)arene such that substantially all of the benzylic halogen thereof is eliminated. Advantageously, such catalytic amounts are within the range from about 0.1 to about 10 weight percent of suitably active Lewis acid based on the weight of (polyhaloalkyl)arene, preferably from about 0.2 to about 3 weight percent of the Lewis acid. The weight of the support is not included in the aforementioned concentrations of Lewis acid. The concentration of the support under such conditions is advantageously in the range from about 1 to 100 weight percent, preferably from about 1 to about 30 weight percent, based on the weight of the (polyhaloalkyl)arene.

In addition to the aforementioned starting ingredients, a solvent such as carbon tetrachloride, ethylene dichloride or similar halohydrocarbons are optionally employed. When used, the solvent is present in an amount between about 0.5 and about 3 liters of solvent per mole of the (polyhaloalkyl)arene.

The dehydrohalogenation reaction is advantageously conducted in the liquid phase at a temperature below 100° C., preferably between about 25° C. and about 80° C., and most preferably between about 55° C. and about 80° C. Preferably, the supported Lewis acid is added to a stirred mixture of the (polyhaloalkyl)arene and the optional solvent. It is sometimes desirable to add the (polyhaloalkyl)arene diluted with solvent to a stirred slurry of the catalyst in solvent. Thus, the rate of hydrogen halide evolution is controlled by the slow addition of reactant.

After the (polyhaloalkyl)arene is contacted with catalyst, the reaction begins immediately, as evidenced by evolution of hydrogen halide gas. The reaction is allowed to proceed to completion while agitating the reaction mixture sufficiently to keep the catalyst in suspension. The reaction pressure is not critical and is conveniently atmospheric.

The product of the dehydrohalogenation reaction is primarily a (haloalkenyl)arene produced by eliminating the benzylic halogen and hydrogen on an adjacent carbon in the (polyhaloalkyl)arene. In embodiments of particular interest, the (polyhaloalkenyl)arene is represented by formula (II):

wherein R, Y and n are as defined hereinbefore. In preferred embodiments of this invention, the dehydrohalogenation is sufficiently selective such that more than 95 mole percent of benzylic halogen is eliminated, most preferably more than 99 mole percent, and less than 5 mole percent of non-benzylic halogen is eliminated most preferably less than 2 mole percent.

The following examples are given to illustrate the invention and should not be construed as limiting its scope. All percentages in the examples are by weight unless otherwise indicated.

EXAMPLE 1

Preparation of 3,5-dichloro-α-methylstyrene
According to U.S. Pat. No. 2,816,934

Chlorine gas is bubbled through 129 g. of 3,5-dichlorotoluene in the presence of light until no further absorption occurs. An increase in weight of 83 g. results. To the product, weighing 212 g., is added dropwise 400 g. of 8 percent fuming sulfuric acid. After being stirred for 30 hours the mixture is poured over cracked ice. The 3,5-dichlorobenzoic acid which precipitated is washed well with water and dried. It weighs 145 g., or 95 percent yield based on the dichlorotoluene.

The acid is converted to 3,5-dichlorobenzoyl chloride in 95 percent yield by treating with 125 g. thionyl chloride. The chloride, weighing 151 g., is then allowed to react with 150 ml. of methyl alcohol and the resulting methyl 3,5-dichlorobenzoate, which when distilled at 120° C.–125° C. at 7 mm. weighs 133 g., or 90 percent of theory. The ester is treated with 2 equivalents of methyl magnesium chloride (125 g.), the Grignard complex hydrolyzed, and the product then dehydrated by refluxing with $NaHSO_4$. The 3,5-dichloro-α-methylstyrene obtained weighs 88 g., or 72 percent of theory based on the ester used, and boiled at 109° C.–111° C. at 12 mm. Its specific gravity is 1.196 and its refractive index is 1.5660, both measured at 25° C.

Addition of $CCl_4$ via U.S. Pat. No. 3,454,657

The 3,5-dichloro-α-methylstyrene is placed in a 250 ml. vessel equipped with a stirring means and a heating means. A mixture including 18.7 g. (0.1 mole) of 3,5-dichloro-α-methylstyrene, as well as 46.2 g. (0.3 mole) of $CCl_4$ and 0.4 g. of cuprous chloride is formed with stirring. To the mixture is added 1.6 g. (0.016 mole) of cyclohexylamine. The mixture is heated to the reflux temperature of $CCl_4$ and maintained at reflux temperature until completion of the reaction in 30 minutes. The reaction mixture is cooled and filtered, and the solvent is removed under vacuum leaving 31.2 g. (91.5 percent yield) of residual product. This residue is recrystallized from hexane to yield essentially pure 1,3-dichloro-5-(2,4,4,4-tetrachlorobutyl)benzene exhibiting a melting point of 44.5°–46.5° C.

Dehydrohalogenation with $AlCl_3$/Silica Gel

A commercially available supported catalyst comprising ~10 percent of $AlCl_3$ and ~90 percent silica gel (~300 micrometers) is added in the amount of 2.5 g. to a mixture consisting of 10.6 g. (0.031 mole) of 1,3-dichloro-5-(2,4,4,4-tetrachlorobutyl)benzene (DCTCB) and 30 ml. of $CCl_4$. The resulting mixture is stirred at room temperature and then heated to 70° C. for a period of 5 hours. Throughout the reaction period, the mixture is stirred at a rate sufficient to maintain the supported catalyst uniformly dispersed throughout the mixture. The reaction mixture is then filtered to remove solid catalyst. The filtrate is placed in a rotary evaporator and evacuated to remove solvent. The residue is an oil which weighs 9.3 g. (0.03 mole) for a 97 percent yield is identified as 3,5-dichloro-α-(2,2,2-trichloroethyl)styrene (DCTCS). Analysis of this residue by GLC shows that it contains ~96 percent of the aforementioned styrene and less than 4 percent of diene represented by the structure:

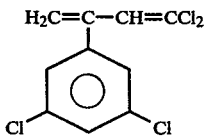

EXAMPLE 2

Dehydrohalogenation with $AlCl_3$/Alumina

A supported catalyst is prepared by slurrying 0.4 g. of $AlCl_3$ and 4.5 g. of alumina (~150 micrometers) in 20 ml. of $CCl_4$ and then stirring the slurry at ~70° C. for one hour. To this slurry at 70° C. is added 250 g. of a mixture of 125 g. of DCTCB and 125 g. of $CCl_4$ in less than 10 minutes. The resulting mixture is heated to 80° C. and maintained there for 4 hours. During this time, the reaction mixture is stirred to maintain the supported catalyst dispersed therein. The reaction mixture is then filtered to remove solid catalyst. The resulting filtrate is evaporated to remove solvent. The remaining oily residue weighs 110 g. (0.355 mole) indicating a yield of ~97 percent of DCTCS. Analysis of this residue by GLC shows that it contains ~97.6 percent of DCTCS and 2.8 percent of the diene.

EXAMPLE 3

Dehydrohalogenation with $TiCl_4$/Alumina

A supported catalyst is prepared by slurrying 0.45 g. of $TiCl_4$ and 4.5 g. of the alumina used in Example 2 in 20 ml. of $CCl_4$ and then stirring the slurry at 70° C. for one hour. To this slurry at 80° C. is added 150 g. of a mixture of 75 g. of DCTCB and 75 g. of $CCl_4$ in less than 10 minutes. The resulting mixture is heated to 80° C. and maintained there for 4 hours. During this time, the reaction mixture is stirred to maintain the supported catalyst uniformly dispersed therein. The reaction mixture is then filtered to remove solid catalyst. The resulting filtrate is evaporated to remove solvent. The remaining oily residue weighs 65.5 g. (0.211 mole) indicating a yield of ~96.5 percent of DCTCS. Analysis of this residue by GLC shows that it contains 95.6 percent of DCTCS and 3.8 percent of the diene.

EXAMPLE 4

Dehydrohalogenation with $SnCl_4$/Alumina

A supported catalyst is prepared by slurrying 0.3 g. of $SnCl_4$ and 3.0 g. of the alumina used in Example 2 in 10 ml. of $CCl_4$ and then stirring the slurry at 70° C. for one hour. DCTCB is then dehydrohalogenated using this supported catalyst according to the procedure of Example 3. Analysis of the resulting dehydrohalogenated product shows that it contains 95.7 percent of DCTCS and 3.4 percent of the diene.

EXAMPLE 5

Dehydrohalogenation with $SbCl_5$/Alumina

A supported catalyst is prepared by slurrying 0.2 g. of $SbCl_5$ and 2.0 g. of alumina (~150 micrometers) in 20 ml. of $CCl_4$ and then stirring the slurry at ~70° C. for one hour.

DCTCB is then dehydrohalogenated using this supported catalyst according to the procedure of Example 3. Analysis of the dehydrohalogenated product shows that it contains 95.1 percent of DCTCS and 2.7 percent of the diene.

What is claimed is:

1. A process for the dehydrohalogenation of a (polyhaloalkyl)arene wherein in the polyhaloalkyl one halogen is a benzylic chlorine or benzylic bromine and at least one halogen is a non-benzylic chlorine or bromine which process comprises contacting said (polyhaloalkyl)arene with a catalytic amount of a suitably active Lewis acid deposited on an inert solid particulate support under dehydrohalogenation conditions in the liquid phase at a temperature below 100° C. such that the benzylic halogen is selectively eliminated to form a (haloalkenyl)arene.

2. A process for the dehydrohalogenation of a (polyhaloalkyl)arene represented by the formula:

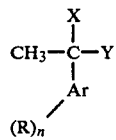

wherein Ar is arene; each R is individually halo, alkyl, aryl, haloalkyl, and haloaryl; X is chloro or bromo; Y is haloalkyl wherein alkyl has 2 or 3 carbons and halo is chloro or bromo; and n is 0 or a whole number from 1 to the maximum number of remaining available ring positions on Ar which process comprises contacting said (polyhaloalkyl)arene with a catalytic amount of a suitably active Lewis acid deposited on an inert particulate support under dehydrohalogenation conditions in the liquid phase at a temperature below 100° C. such that X is selectively eliminated to form a (haloalkenyl)arene represented by the formula:

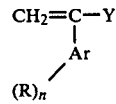

in which Y, Ar, R and n are as defined herein.

3. The process of claim 2 wherein each R is individually halo, alkyl, haloalkyl, aryl or haloaryl, Y is polyhaloalkyl and n is 0, 1 or 2.

4. The process of claim 2 wherein (polyhaloalkyl)arene is (polyhaloalkyl)benzene represented by the structural formula:

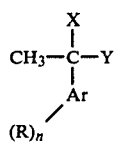

wherein R is Cl, Br, F, or alkyl having 1 to 4 carbons; Y is haloalkyl represented by the formula:

$$-CH_2-\underset{\underset{R'}{|}}{\overset{\overset{X'}{|}}{C}}-R'$$

wherein X' is Cl or Br, each R' is individually H, Cl or Br; and n is 0 to 2.

5. The process of claim 3 wherein the Lewis acid is $AlCl_3$, $SbCl_5$, $SbCl_3$, $TiCl_4$ or $SnCl_4$ and the solid support is alumina.

6. The process of claim 5 wherein the (polyhaloalkyl)benzene is 1,3-dichloro-5-(2,4,4,4-tetrachlorobutyl)benzene and the dehydrohalogenation is carried out in the presence of from about 0.1 to about 10 weight percent of $AlCl_3$ and from about 1 to about 100 weight percent of alumina, both percentages being based on the weight of (polyhaloalkyl)benzene, at a reaction temperature in the range from about 25° to about 80° C., said alumina having an average particle diameter in the range from about 100 to about 400 micrometers.

* * * * *